US00PP26386P3

(12) United States Plant Patent
Brandsma

(10) Patent No.: US PP26,386 P3
(45) Date of Patent: Feb. 2, 2016

(54) *HAWORTHIA* PLANT NAMED 'SEASTAR'

(50) Latin Name: *Howorthia limifolia×fasciata*
Varietal Denomination: SEASTAR

(71) Applicant: Christine Brandsma, Moshi (TZ)

(72) Inventor: Christine Brandsma, Moshi (TZ)

( * ) Notice: Subject to any disclaimer, the term of this patent is extended or adjusted under 35 U.S.C. 154(b) by 88 days.

(21) Appl. No.: 13/999,379

(22) Filed: Feb. 18, 2014

(65) Prior Publication Data

US 2015/0237787 P1 Aug. 20, 2015

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Haworthia* cultivar named 'SEASTAR' is disclosed, characterized by medium sized, compact plants, with a more open center, and strong heat and drought resistance. Foliage is strong and consistently green with abundant white spots. The new variety is an *Haworthia*, typically produced as an ornamental plant.

1 Drawing Sheet

Latin name of the genus and species: *Haworthia limifolia× fasciata.*
Variety denomination: 'SEASTAR'.

BACKGROUND OF THE INVENTION

The new cultivar is a product of a planned breeding program. The objectives of the planned breeding program were to develop new *Haworthia* varieties with interesting foliage for ornamental purposes. The breeding program was developed under the direction of the inventor, Christine Brandsma, in Moshi, Tanzania. The new variety originated from a cross pollination of the unpatented commercial variety *Haworthia limifolia* seed parent and the pollen parent, the unpatented commercial variety, *Haworthia fasciata*. 'Big Band' The crossing was made during January of 2009.

The new variety was selected by the inventor Christine Brandsma, in February of 2010 in a group of seedlings resulting from the crossing. The new cultivar was selected in a commercial greenhouse in Moshi, Tanzania.

Asexual reproduction of the new cultivar 'SEASTAR' was first performed at a commercial greenhouse in Tanzania by vegetative cuttings in March 2011. The additional generation produced vegetative cuttings have shown that the unique features of this cultivar are stable and reproduced true to type.

SUMMARY OF THE INVENTION

The cultivar 'SEASTAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SEASTAR'. These characteristics in combination distinguish 'SEASTAR' as a new and distinct *Haworthia* cultivar:

1. Less growth from center, forming a plant with a more open center.
2. Heat and drought resistance.

3. Plant size is medium, growth compact.
4. Abundant white dots on upper and lower foliage.
5. Even light green coloration.
6. Leaf apex is not as sharp as typical of *Haworthia.*
7. Comparatively longer leaf length and broader width.
8. Strong and stiff foliage.
9. Slow growth
10. Slow rooting.

PARENT COMPARISON

Plants of the new cultivar 'SEASTAR' are similar to the unpatented, unnamed, proprietary variety of *Haworthia limifolia* seed parent in most horticultural characteristics. The new variety however differs in the following characteristics:

1. Longer and wider leaves.
2. Less sharp leaf point.
3. White dots on foliage. Seed parent has no white dots.
4. Not striped, Seed parents has green stripes on the upper and lower leaf surface.
5. Larger plant size.
6. Fewer leaves.
7. More growth from center.

Plants of the new cultivar 'SEASTAR' are similar to the pollen parent, an unpatented, unnamed, proprietary variety of *Haworthia fasciata* 'Big Band' in most horticultural characteristics. The new variety however differs in the following characteristics:

1. Slightly larger leaves.
2. Less sharply pointed leaves.
3. No white striping. Pollen parent has strong white stripe on the underside of leaves.
4. No green striping. Pollen parent has green striping on the upper and lower leaf surface.
5. More compact size.
6. Stronger foliage.
7. Faster rooting.
8. More growth from center.
9. Greater heat resistance.

COMMERCIAL COMPARISON

'SEASTAR' can be compared to the unpatented commercial variety *Haworthia fasciata* 'Con Color'. Plants of 'Con Color' are similar to plants of 'SEASTAR' in most horticultural characteristics. However 'SEASTAR' differs from 'Con Color' in the following characteristics:

1. Larger leaf size.
2. Less sharp leaf point.
3. More striking white dots. More dots, of a brighter white.
4. Leaves more even green coloration.
5. Larger plant size.
6. Slower rooting.
7. Less heat resistant.

'SEASTAR' can also be compared to the unpatented commercial variety *Haworthia fasciata*. Plants of *Haworthia fasciata* are similar to plants of 'SEASTAR' in most horticultural characteristics. However 'SEASTAR' differs from *Haworthia fasciata* in the following characteristics:

1. Larger leaf size.
2. Less sharp leaf point.
3. The white dots are more pustulate.
4. Different leaf coloration.
5. Larger plant size.
6. Less center growth.
7. White dots on upper side of leaf. The comparator has hardly any dots or stripes on upper leaf surface.

BRIEF DESCRIPTION OF THE PHOTOGRAPH

The accompanying photograph in FIG. 1 illustrates in full color typical plants of 'SEASTAR' grown in a greenhouse in Moshi, Tanzania. This plants are approximately 2 years old, shown in a 13 cm pots. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SEASTAR' plants grown in a greenhouse in Moshi, Tanzania. Temperatures ranged from 10° C. to 20° C. at night to 20° C. to 32° C. during the day. No artificial light, photoperiodic treatments were given to the plants. Measurements and numerical values represent averages of typical plant types.

Botanical classification: *Haworthia limifolia×fasciata* 'SEASTAR'.

PROPAGATION

First propagation method: Vegetative, with cuttings.

Type of propagation typically used: Vegetative, with cuttings.

Time to initiate roots: About 30 days at approximately 20° C.

Time to produce rooted plantlet: Approximately 50 weeks at approximately 25° C.

Root description: Thick roots, moderately branched. Colored near RHS Orange-White 159A and 159C.

PLANT

Growth habit: Upright rosette, then with maturity side shoots rosettes.

Plant shape: Cylindrical.

Height: Approximately 15 cm to top of highest leaf.

Plant spread: Approximately 15 cm in a 5 inch pot.

Growth rate: Moderate, compared to other *Haworthia*.

Branching characteristics (if any):

*Lateral branches*.—Side shoots are rosettes, no lateral branches. Diameter: Average 2 cm. Length: Average 5 cm. Color: Near RHS Green 137A, dots White 155D. Angle: Approximately 150° angle from base.

FOLIAGE

Leaf:

*Arrangement*.—Cylindrical.

*Average length*.—Approximately 5 to 8 cm.

*Average width*.—Approximately 2 cm.

*Shape of blade*.—Narrow deltate.

*Apex*.—Acute.

*Base*.—4 cm.

*Texture of top surface*.—Rough.

*Texture of bottom surface*.—Rough.

*Quantity of leaves per plant*.—Approximately 12 to 16.

*Color*.—Young foliage upper side: Near RHS Green 137D with spots, near White 155D. Young foliage under side: Near RHS Green 137D with spots, near White 155D. Mature foliage upper side: Near RHS Green 137D with spots, near White 155D. Mature foliage under side: Near RHS Green 137D with spots, near White 155D.

*Venation*.—Type: Linear. Venation color upper side: Indistinguishable from leaf blade. Venation color under side: Indistinguishable from leaf blade.

INFLORESCENCE

Flowering has not been observed to date.

OTHER CHARACTERISTICS

Disease and pest resistance: Neither resistance nor susceptibility to the normal diseases and pests of *Haworihia* has been observed.

Drought tolerance and cold tolerance: The new cultivar of *Haworthia*, is tolerant of temperatures from approximately 0° C. to 40° C.

Fruit/seed production: Not observed to date.

What is claimed is:

1. A new and distinct cultivar of *Haworthia* plant named 'SEASTAR' as herein illustrated and described.

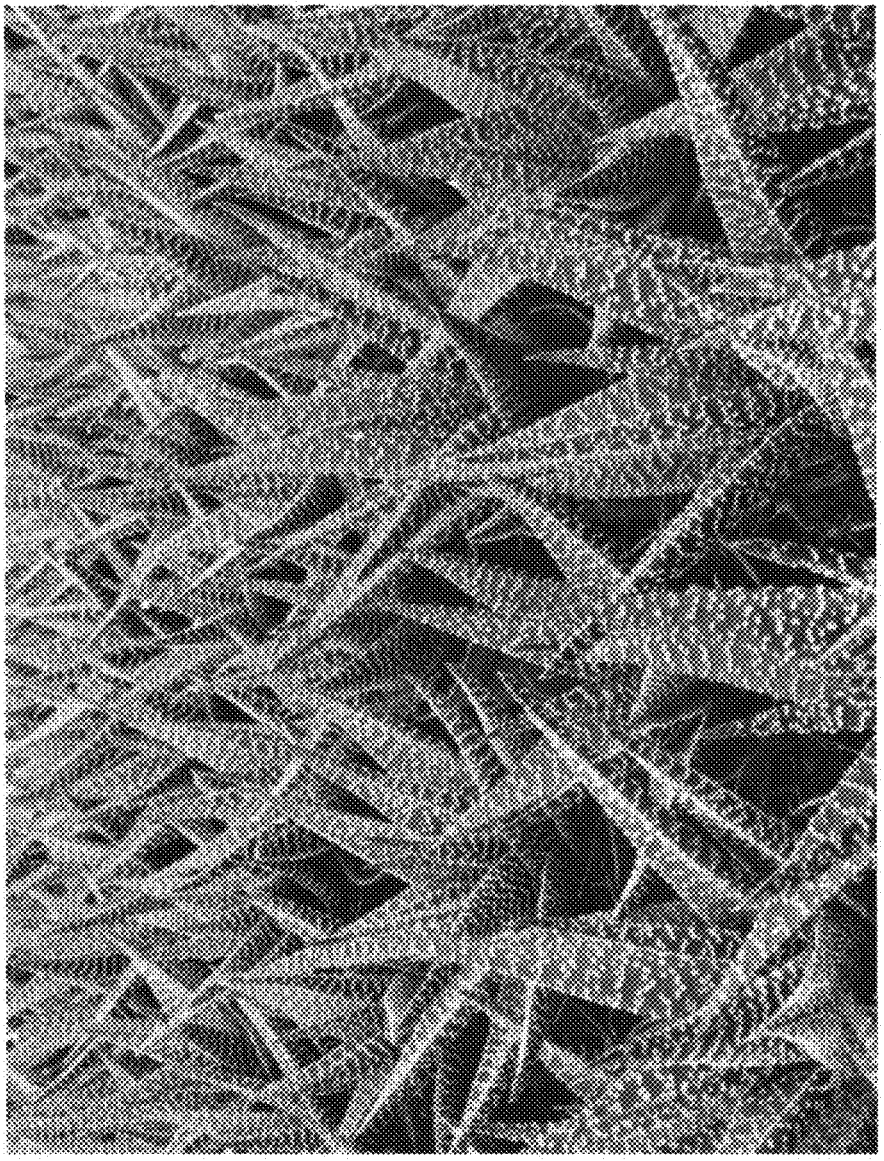

* * * * *